United States Patent
Sparks et al.

(10) Patent No.: US 9,074,244 B2
(45) Date of Patent: Jul. 7, 2015

(54) ARRAY-BASED TRANSLOCATION AND REARRANGEMENT ASSAYS

(75) Inventors: Andrew Sparks, Los Gatos, CA (US); Michael H. Shapero, Redwood City, CA (US); Glenn K. Fu, Dublin, CA (US); Keith W. Jones, Sunnyvale, CA (US)

(73) Assignee: Affymetrix, Inc., Santa Clara, CA (US)

( * ) Notice: Subject to any disclaimer, the term of this patent is extended or adjusted under 35 U.S.C. 154(b) by 840 days.

(21) Appl. No.: 12/402,486

(22) Filed: Mar. 11, 2009

(65) Prior Publication Data

US 2009/0239764 A1 Sep. 24, 2009

Related U.S. Application Data

(60) Provisional application No. 61/035,697, filed on Mar. 11, 2008.

(51) Int. Cl.
  *C12Q 1/68* (2006.01)
  *C07H 21/00* (2006.01)
(52) U.S. Cl.
  CPC .................................. *C12Q 1/6827* (2013.01)
(58) Field of Classification Search
  CPC ...... C12Q 1/68; C12Q 1/6813; C12Q 1/6876; C07H 21/00
  USPC ..................... 435/6; 536/23.1, 24.3
  See application file for complete search history.

(56) References Cited

U.S. PATENT DOCUMENTS

| | | | |
|---|---|---|---|
| 4,675,283 A | 6/1987 | Roninson | |
| 4,683,195 A | 7/1987 | Mullis et al. | |
| 4,683,202 A | 7/1987 | Mullis | |
| 4,800,159 A | 1/1989 | Mullis et al. | |
| 5,002,867 A | 3/1991 | Macevicz | |
| 5,093,245 A | 3/1992 | Keith et al. | |
| 5,102,785 A | 4/1992 | Livak et al. | |
| 5,143,854 A | 9/1992 | Pirrung | |
| 5,202,231 A | 4/1993 | Drmanac | |
| 5,366,877 A | 11/1994 | Keith | |
| 5,387,505 A | 2/1995 | Wu | |
| 5,436,142 A | 7/1995 | Wigler et al. | |
| 5,470,737 A | 11/1995 | Weinshilboum et al. | |
| 5,487,985 A | 1/1996 | McClelland et al. | |
| 5,492,806 A | 2/1996 | Drmanac et al. | |
| 5,501,964 A | 3/1996 | Wigler et al. | |
| 5,508,169 A | 4/1996 | Deugau et al. | |
| 5,508,178 A | 4/1996 | Rose et al. | |
| 5,512,439 A | 4/1996 | Hornes et al. | |
| 5,525,464 A | 6/1996 | Drmanac | |
| 5,565,340 A | 10/1996 | Chenchik et al. | |
| 5,578,467 A | 11/1996 | Schuster et al. | |
| 5,580,730 A | 12/1996 | Okamoto | |
| 5,582,989 A | 12/1996 | Caskey et al. | |
| 5,597,694 A | 1/1997 | Munroe et al. | |
| 5,612,180 A | 3/1997 | Brown et al. | |
| 5,624,825 A | 4/1997 | Walker et al. | |
| 5,667,972 A | 9/1997 | Drmanac | |
| 5,695,937 A * | 12/1997 | Kinzler et al. | 435/6 |
| 5,695,940 A | 12/1997 | Drmanac | |
| 5,700,637 A | 12/1997 | Southern | |
| 5,700,642 A | 12/1997 | Monforte et al. | |
| 5,710,000 A | 1/1998 | Sapolsky et al. | |
| 5,710,028 A | 1/1998 | Eyal et al. | |
| 5,712,127 A | 1/1998 | Malek et al. | |
| 5,759,822 A | 6/1998 | Chenchik et al. | |
| 5,763,239 A | 6/1998 | Short et al. | |
| 5,776,753 A | 7/1998 | Hillman et al. | |
| 5,807,522 A | 9/1998 | Brown et al. | |
| 5,837,832 A | 11/1998 | Chee et al. | |
| 5,851,770 A | 12/1998 | Babon et al. | |
| 5,854,033 A | 12/1998 | Lizardi | |
| 5,858,656 A | 1/1999 | Deugau et al. | |
| 5,861,242 A | 1/1999 | Chee et al. | |
| 5,876,929 A | 3/1999 | Wigler et al. | |
| 5,888,737 A | 3/1999 | DuBridge et al. | |
| 5,968,740 A | 10/1999 | Fodor et al. | |
| 5,972,693 A * | 10/1999 | Rothberg et al. | 435/287.2 |
| 5,994,068 A | 11/1999 | Guilfoyle et al. | |
| 6,001,574 A | 12/1999 | Short et al. | |
| 6,004,783 A | 12/1999 | Ausubel et al. | |
| 6,013,445 A | 1/2000 | Albrecht et al. | |

(Continued)

FOREIGN PATENT DOCUMENTS

| | | |
|---|---|---|
| CA | 2036946 | 10/2001 |
| EP | 0224126 | 6/1987 |

(Continued)

OTHER PUBLICATIONS

Dunn et al., Genomic signature tags (GSTs): a system for profiling genomic DNA. Genome Research 12 : 1756-1765 (2002).*

Hultman et al., Bidirectional solid-phase sequencing of in vitro—amplified plasmid DNA. Biotechniques 10 (1) : 84-93 (1991).*

Innis et al., DNA sequencing with *Thermus aquaticus* DNA polymerase and direct sequencing of polymerase chain reaction-amplified DNA. PNAS 85 : 9436-9440 (1988).*

(Continued)

*Primary Examiner* — Ethan C Whisenant

(74) *Attorney, Agent, or Firm* — Banner & Witcoff, Ltd.

(57) ABSTRACT

Methods for detecting genomic rearrangements are provided. In one embodiment, methods are provided for the use of paired end tags from restriction fragments to detect genomic rearrangements. Sequences from the ends of the fragments are brought together to form ditags and the ditags are detected. Combinations of ditags are detected by an on-chip sequencing strategy that is described herein, using inosine for de novo sequencing of short segments of DNA. In another aspect, translocations are identified by using target specific capture and analysis of the captured products on a tiling array.

12 Claims, 5 Drawing Sheets

(56) References Cited

U.S. PATENT DOCUMENTS

| | | | |
|---|---|---|---|
| 6,027,877 | A | 2/2000 | Wagner et al. |
| 6,027,894 | A | 2/2000 | Sapolsky et al. |
| 6,027,945 | A | 2/2000 | Smith et al. |
| 6,033,861 | A | 3/2000 | Schafer et al. |
| 6,045,994 | A | 4/2000 | Zabeau et al. |
| 6,060,240 | A | 5/2000 | Kamb et al. |
| 6,060,245 | A | 5/2000 | Sorge et al. |
| 6,100,030 | A | 8/2000 | McCasky Feazel et al. |
| 6,103,463 | A | 8/2000 | Chetverin |
| 6,107,023 | A | 8/2000 | Reyes et al. |
| 6,124,090 | A | 9/2000 | Rose et al. |
| 6,156,502 | A | 12/2000 | Beattie |
| 6,197,510 | B1 | 3/2001 | Vinayagamoorthy |
| 6,197,557 | B1 | 3/2001 | Makarov et al. |
| 6,232,066 | B1 | 5/2001 | Felder et al. |
| 6,232,067 | B1 | 5/2001 | Hunkapiller et al. |
| 6,238,884 | B1 | 5/2001 | Short et al. |
| 6,258,539 | B1 | 7/2001 | Hunkapiller et al. |
| 6,277,606 | B1 | 8/2001 | Wigler et al. |
| 6,280,950 | B1 | 8/2001 | Lipshutz et al. |
| 6,287,825 | B1 | 9/2001 | Weissman et al. |
| 6,291,181 | B1 | 9/2001 | Sapolsky et al. |
| 6,306,643 | B1 | 10/2001 | Gentalen et al. |
| 6,322,971 | B1 | 11/2001 | Chetverin et al. |
| 6,355,431 | B1 | 3/2002 | Chee et al. |
| 6,361,947 | B1 | 3/2002 | Dong et al. |
| 6,365,352 | B1 | 4/2002 | Yerramilli et al. |
| 6,368,799 | B1 | 4/2002 | Chee |
| 6,472,185 | B2 | 10/2002 | McCasky Feazel et al. |
| 6,509,160 | B1 | 1/2003 | Sapolsky et al. |
| 6,514,768 | B1 | 2/2003 | Guire et al. |
| 6,632,611 | B2 | 10/2003 | Su et al. |
| 6,703,228 | B1 | 3/2004 | Landers et al. |
| 6,720,179 | B1 | 4/2004 | Macevicz |
| 6,773,885 | B1 | 8/2004 | Walder et al. |
| 6,773,886 | B2 | 8/2004 | Kaufman et al. |
| 6,812,005 | B2 | 11/2004 | Fan et al. |
| 6,872,529 | B2 | 3/2005 | Su |
| 6,958,217 | B2 | 10/2005 | Pedersen |
| 6,958,225 | B2 | 10/2005 | Dong |
| 7,108,976 | B2 | 9/2006 | Jones et al. |
| 7,267,966 | B2 | 9/2007 | Dong et al. |
| 7,588,889 | B2 | 9/2009 | Wolber et al. |
| 7,662,559 | B2 | 2/2010 | Sapolsky et al. |
| 7,745,178 | B2 | 6/2010 | Dong |
| 2002/0065609 | A1* | 5/2002 | Ashby ............... 702/20 |
| 2003/0059815 | A1 | 3/2003 | Sapolsky et al. |
| 2004/0096892 | A1* | 5/2004 | Wang et al. ......... 435/6 |
| 2004/0110183 | A1* | 6/2004 | Ashby ................ 435/6 |
| 2004/0265842 | A1 | 12/2004 | Sapolsky et al. |
| 2005/0095645 | A1* | 5/2005 | Jones et al. ......... 435/6 |
| 2006/0057586 | A1* | 3/2006 | Sung et al. ......... 435/6 |
| 2006/0063158 | A1 | 3/2006 | Dong et al. |
| 2006/0068415 | A1 | 3/2006 | Jones et al. |
| 2006/0223097 | A1 | 10/2006 | Sapolsky et al. |
| 2006/0281097 | A1* | 12/2006 | Chiu et al. ......... 435/6 |
| 2007/0161024 | A1* | 7/2007 | Ng et al. ............ 435/6 |
| 2009/0137402 | A1* | 5/2009 | Wang et al. ......... 506/2 |
| 2009/0156431 | A1* | 6/2009 | Lok ................. 506/26 |
| 2009/0325239 | A1* | 12/2009 | Lok ............... 435/91.2 |
| 2010/0028888 | A1* | 2/2010 | Smith et al. ......... 435/6 |
| 2010/0292097 | A1* | 11/2010 | Dong ................ 506/9 |
| 2010/0323361 | A1* | 12/2010 | Pugh et al. ......... 435/6 |
| 2011/0009276 | A1* | 1/2011 | Vermaas et al. ..... 506/7 |

FOREIGN PATENT DOCUMENTS

| | | |
|---|---|---|
| EP | 1001037 | 5/2000 |
| EP | 0630972 | 8/2000 |
| EP | 0735144 | 6/2002 |
| EP | 1350853 | 10/2003 |
| EP | 0534858 | 4/2005 |
| EP | 1124990 | 1/2006 |
| WO | WO 89/10977 | 11/1989 |
| WO | WO 89/12695 | 12/1989 |
| WO | WO 90/08821 | 8/1990 |
| WO | WO 90/15070 | 12/1990 |
| WO | WO 91/05861 | 5/1991 |
| WO | WO 91/18114 | 11/1991 |
| WO | WO 92/10092 | 6/1992 |
| WO | WO 93/22457 | 11/1993 |
| WO | WO 95/11995 | 5/1995 |
| WO | WO 98/20165 | 5/1998 |
| WO | WO 98/41657 | 9/1998 |
| WO | WO 99/23256 | 5/1999 |
| WO | WO 99/36571 | 7/1999 |
| WO | WO 99/43853 | 9/1999 |
| WO | WO 00/18960 | 4/2000 |
| WO | WO 00/78975 | 12/2000 |
| WO | WO 01/75163 | 10/2001 |
| WO | WO 01/88174 | 11/2001 |
| WO | WO 02/20844 | 3/2002 |

OTHER PUBLICATIONS

Korbel et al., Paired-End Mapping Reveals Extensive Structural variation in the human genome. Science 318 : 420-426 (2007).*
Matsumura et al., Gene Expression analysis of plant host-pathogen interactions by SuperSAGE. PNAS 100 : 15718-15723 (2003).*
Michalatos-Beloin et al., Molecular haplotyping of genetic markers 10kb apart by allele-specific long-range PCR. Nucleic Acids Research 24 (3) : 4841-4843 (1996).*
Ng et al. Multiplex sequencing of paired-end ditags ( MS-PET): a strategy for the ultra-high-throughput analysis of transcriptomes and genomes. Nucleic Acids Research 34 (12) : e84 (2006).*
Ruan et al., Fusion transcripts and transcribed retrotransposed loci discovered through comprehensive transcriptome analysis using Paired-End diTags (PETs). Genome Research 17 L 828/-838 (2007).*
Wang et al., Digital Karyotyping. PNAS 99(25) : 16156-16161 (2002).*
Warren et al. Physical map-assisted whole-genome shotgun sequence assemblies. Genome Research 16 : 768-775 (2006).*
Wimmer et al., Combined restriction landmark genomic scanning and virtual genome scans identify a novel human homeobox gene, ALX3, that is hypermethylated in neuroblastoma. Genes, Chromosomes & Cancer 33 : 285-294 (2002).*
Tuzun et al., Fine-scale structural variations of the human genome. Nature Genetics 37 (7) : 727732 (Jul. 2005).*
Jongeneel et al., An atlas of human gene expression from massively parrallel signature sequencing (MPSS). Genome Resarch 15 : 1007-1014 (2005).*
Margulies et al., Genome sequencing in microfabricated high density picolitre reactors. Nature 437 : 376-380 (2005).*
U.S. Appl. No. 08/082,937, filed Jun. 1993, Fodor.
U.S. Appl. No. 08/143,312, filed Oct. 1993, Chee.
U.S. Appl. No. 08/284,064, filed Aug. 1994, Chee.
U.S. Appl. No. 08/307,881, filed Sep. 1994, Sapolsky.
U.S. Appl. No. 12/272,680, filed Nov. 2008, Sapolsky.
U.S. Appl. No. 12/822,896, filed Jun. 2010, Dong.
Barrett et al., "Genotypic Analysis of Multiple Loci in Somatic Cells by Whole Genome Amplification," Nucleic Acids Research, vol. 23, No. 17, pp. 3488-3492 (1995).
Brenner et al., "DNA fingerprinting by sampled sequencing," Proc. Natl. Acad. Sci., 86:8902-8906 (1989).
Broude et al., "High-Level Multiplex DNA Amplification," Antisense & Nculeic Acid Drug Development, 11: 327-332 (2001).
Broude et al., "Multiplex Allele-Specific Target Amplification Based on PCR Suppression," PNAS, vol. 98, No. 1, pp. 206-211 (Jan. 2001).
Cease et al., "A vector for facile PCR product cloning and modification generating any desired 4-base 5' overhang: pRPM," Biotechniques, 14: 250-255 (1993).
Chee et al., "Accessing Genetic Information with High-Density DNA Arrays," Science, 274:610-614 (1996).
DeRisi et al., "Exploring the Metabolic and Genetic Control of Gene Expression of a Genomic Scale," Science, vol. 278, pp. 680-686 (1997).

(56) References Cited

OTHER PUBLICATIONS

Geng et al., "Isolation of differentially expressed genes by combining representational difference analysis (RDA) and cDNA library arrays," Biotechniques, vol. 25, No. 3, pp. 434-438 (1998).

Guilfoyle et al., "Ligation-mediated PCR amplification of specific fragments from class-II restriction endonuclease total digest," Nucleic Acids Research, vol. 9, No. 25, pp. 1854-1858 (1997).

Hoheisel, "Application of hybridization techniques to genome mapping and sequencing," Trends in Genetics, 10(3): 79-83 (1994).

Kalisch, "Covalently linked sequencing primer linkers (splinkers) for sequence analysis of restriction fragments," Gene, vol. 44, pp. 263-270 (1986).

Kinzler and Vogelstein, "Whole genome PCR: application to the identification of sequences bound by gene regulatory proteins," Nucleic Acids Research, 17(10): 3645-53 (1989).

Lipshutz et al., "Using Oligonucleotide Probe Arrays to Access Genetic Diversity," Biotechniques, vol. 19, No. 3, pp. 442-447 (1995).

Lisitsyn et al, "Cloning the differences between two complex genomes," Science, 259: 946-51 (1993).

Lucito et al., "Genetic Analysis Using Genomic Representations," Proc. National Academy of Sciences, vol. 95, pp. 4487-4492 (Apr. 1998).

Lukyanov et al., "Construction of cDNA Libraries from Small Amounts of Total RNA Using the Suppression PCR Effect," Biochemical and Biophysical Research Communications, vol. 230, No. 2, pp. 285-288 (1997).

Lukyanov et al., "Inverted Terminal Repeats Permit the Average Length of Amplified DNA Fragments to be Regulated During Preparation of cDNA Libraries by Polymerase Chain Reaction," Analytical Biochemistry, vol. 229, No. 2, pp. 198-202 (1995).

Moyer et al., "A computer-simulated restriction fragment length polymorphism analysis of bacterial small-subunit rRNA genes: Efficacy of selected tetrameric restriction enzymes for studies of microbial diversity in nature," Applied and Environmental Microbiology, vol. 62, No. 7, pp. 2501-2507 (1996).

New England Biolabs, Inc., "Frequencies of Restriction Sites," www.neb.com, Jul. 18, 2002.

New England Biolabs, Inc., Swa I and Pme I product data sheets, www.neb.com, Jul. 13, 2000 and Apr. 1, 2000.

Ng et al., "Paired-End diTagging for Transcriptome and Genome Analysis," Current Protocols in Molecular Biology, 21.12.1-21.12.42, Supplement 79, Wiley Interscience (Jul. 2007).

Patent Interference No. 105,439, *Landers* v. *Sapolsky*.

Roux and Dhanarajan, "A Strategy for Single Site PCR Amplification of dsDNA: Priming Digested Cloned on Genomic DNA from an Anchor-Modified Restriction Site and a Short Internal Sequence," BioTechniques, vol. 8, No. 1, pp. 48-57 (1990).

Sapolsky and Lipshutz, "Mapping genomic library clones using oligonucleotide arrays," Genomics, 33: 445-456 (1996).

Shagin et al., "Regulation of Average Length of Complex PCR Product," Nucleic Acids Research, vol. 27, No. 18, e23 (1999).

Siebert et al., "An Improved PCR Method for Walking an Uncloned Genomic DNA," Nucleic Acids Research, vol. 23, No. 6, pp. 1087-1088 (1995).

Smith, "Ligation-mediated PCR of restriction fragments from large DNA molecules," PCR Methods and Applications, 2: 21-27 (1992).

Szybalski et al., "Class-IIS restriction enzymes—a review," Gene, 100: 13-26 (1991).

Szybalski, "Universal restriction endonucleases: designing novel cleavage specificities by combining adapter oligodeoxynucleotide and enzyme moieties," Gene, 40: 169-173 (1985).

Unrau et al., "Non-cloning amplification of specific DNA fragments from whole genomic DNA digest using DNA indexers," Gene, 145: 163-169 (1994).

Vos et al., "AFLP: A New Technique for DNA Fingerprinting," Nucleic Acids Research, vol. 23, No. 21, pp. 4407-4414 (1995).

Wagner and Radman, "Mismatch binding protein-based mutation detection systems," Methods: a Companion to Methods in Enzymology, vol. 7, pp. 199-203 (1995).

Wikipedia, TaqMan probes, Sep. 28, 2010.

Chiu et al. (2006) PET-Tool: a software suite for comprehensive processing and managing of paired-end diTag (PET) sequence data. Bio. Med. Central, http://www.biomedcentral.com/1471-2105/7/390.

Ng et al. (2005) Gene identification signature (GIS) analysis for transcriptome characterization and genome annotation. Nature Meth. 2, 105-111.

Ng et al. (2006) Muliplex sequencing of paired-end ditags (MS-PET): a strategy for ultra-high-throughput analysis of transcriptomes and genomes. Nucleic Acids Research. vol. 34, No. 12, e84.

Wei et al. (2006) A global map of p53 transcription-factor binding sites in the human genome. Cell 124, pp. 207-219, Elsevier, Inc.

* cited by examiner

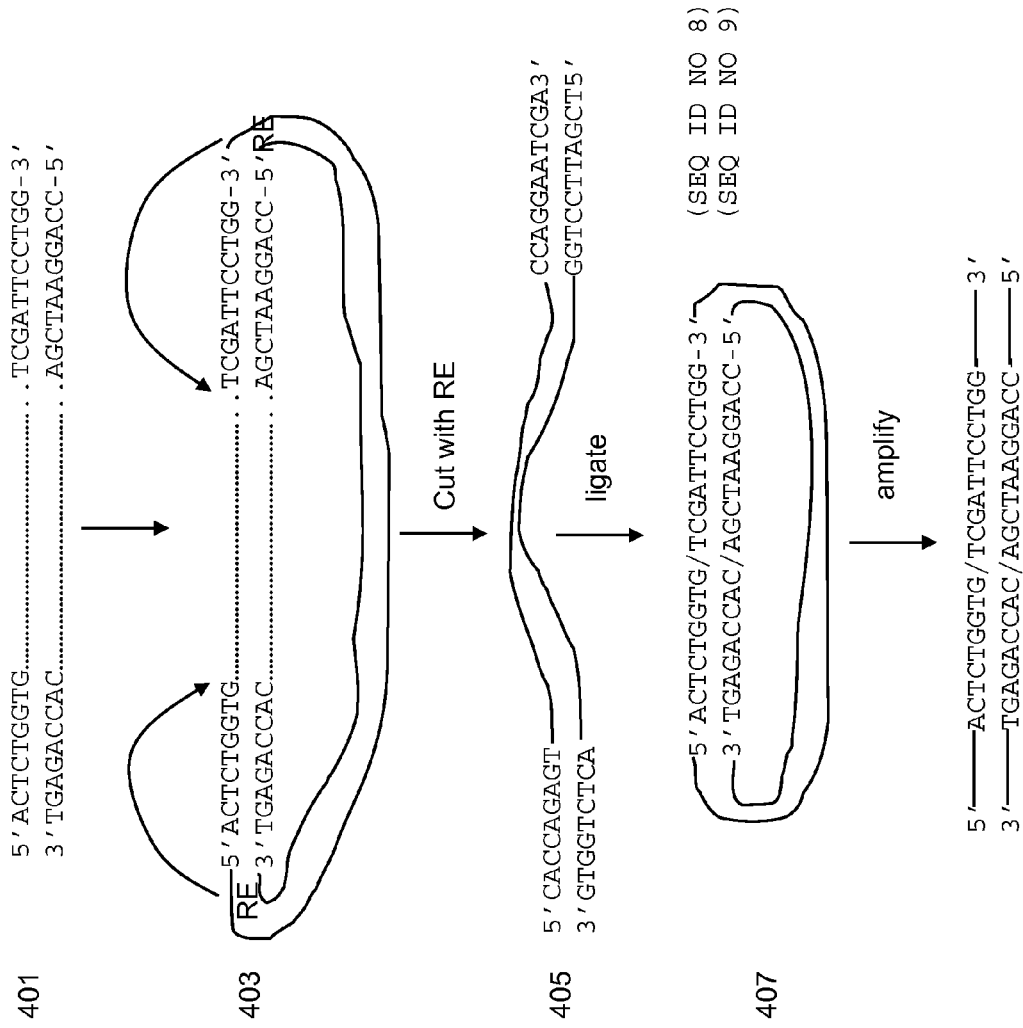

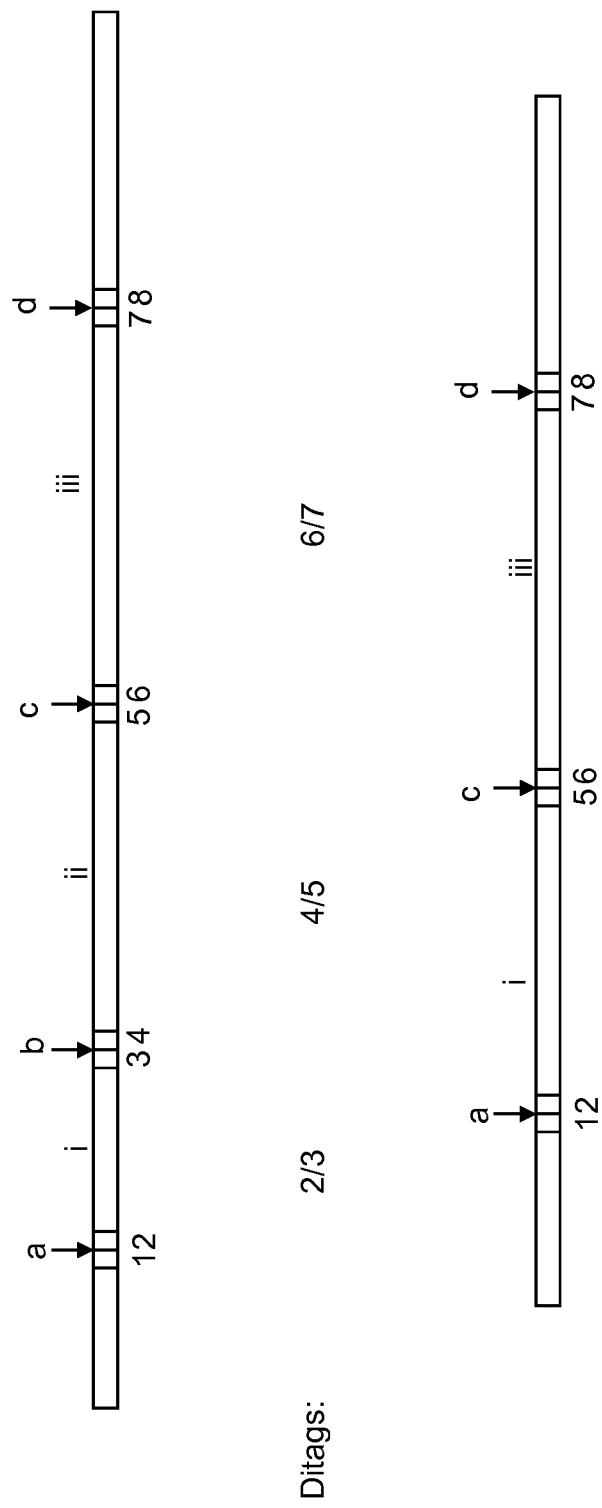

ARRAY-BASED TRANSLOCATION AND REARRANGEMENT ASSAYS

RELATED APPLICATIONS

This application claims the benefit of U.S. Provisional Application No. 61/035,697, filed Mar. 11, 2008, the entire contents of which are hereby incorporated by reference.

FIELD OF THE INVENTION

The methods of the invention relate generally to detection of chromosomal rearrangements and translocations using hybrid selection and tiling arrays.

BACKGROUND OF THE INVENTION

A chromosome translocation is a chromosome abnormality caused by rearrangement of parts between nonhomologous chromosomes. A fusion gene may be created when the translocation joins two otherwise separated genes, an event which is common in cancer. Cytogenetics and karyotyping of affected cells may be used to detect translocations. There are two main types, reciprocal (also known as non-Robertsonian) and Robertsonian. Also, translocations can be balanced and result in an even exchange of material with no genetic information extra or missing, or unbalanced, having an unequal exchange of chromosome material and sometimes resulting in extra or missing genes or portions thereof. Chromosomal rearrangements are known to contribute to a variety of diseases in humans.

Translocations and inversions are structural abnormalities; other types of chromosomal abnormalities include numerical or copy number changes, for example, extra or missing chromosomes or chromosomal regions and large-scale deletions or duplications. Structural abnormalities can arise from errors during homologous recombination. Both structural and numerical abnormalities can occur in gametes and therefore will be present in all cells of an affected person's body, or they can occur during mitosis and give rise to a genetic mosaic individual who has some normal and some abnormal cells.

SUMMARY OF THE INVENTION

In a first aspect, methods are provided for assaying a diploid sample for the presence of a translocation, by assessing whether the sample contains at least one DNA molecule consisting of sequences normally affiliated with two different chromosomes. This method entails specifically capturing and amplifying one chromosome from a sample by hybrid selection, and assaying the captured material for the presence of other chromosomes by hybridizing the captured material to a whole-genome tiling array.

In another aspect methods are provided for assaying a diploid sample for the presence of large-scale rearrangements, including insertions, deletions, translocations, and inversions, by globally assessing whether the ends of restrictions fragments from a sample have been rearranged with respect to each other and their position in the reference sequence of the human genome.

The methods accomplish this via the following steps, which will be described in more detail below.

First, digest a genomic DNA of interest with a restriction enzyme, and then generate a population of "paired-end ditags", each of which is derived from a different restriction fragment, and each of which contains an approximately 18 bp tag from the left terminus of the restriction fragment coupled directly to an approximately 18 bp tag from the right terminus of the restriction fragment.

Second, hybridize the population of ditags to a "ditag sequencing array", designed to capture every tag on the array, and to generate enough sequence information regarding each of the captured tags' ditag mates to determine the identity of all ~500K ditags in the sample. Perform the on-chip chemistry necessary to determine the identities of all ditags in the sample. Compare the sample's ditags with those predicted from the human genome. Variant ditags indicate restriction fragments containing rearrangements with respect to the reference sequence of the human genome.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 4 provides an example of the resulting orientation of the tag sequences resulting from the method of FIG. 1.

FIG. 5 illustrates the expected combinations of ditag from a genomic region in the upper panel and the expected ditags from the same region following a deletion of a region.

Figure 1:
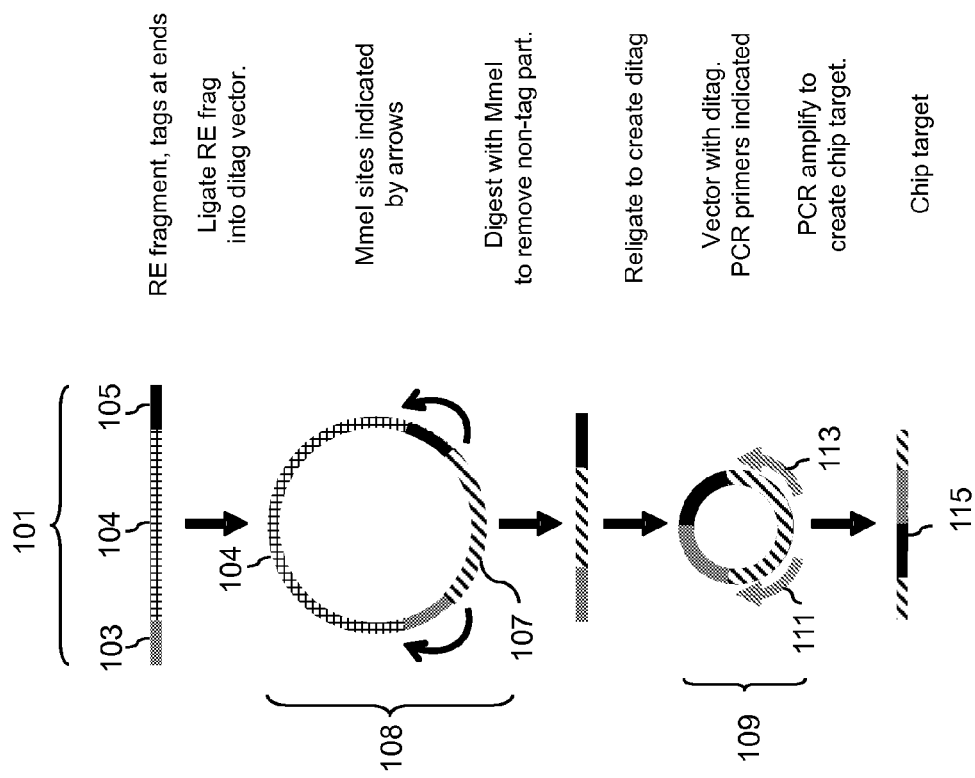
FIG. 1 shows an exemplary sample prep process.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), Lehninger, *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, now abandoned, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes. Additional methods for nucleic acid array synthesis are disclosed in US 20070161778, Kuimelis et al. which describes the use of acid scavengers in array synthesis and U.S. Pat. No. 6,271,957 which describes methods for array synthesis where areas are activated by spatial light modulation and without the use of a photomask. Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GENE-CHIP®. Example arrays are shown on the website at affymetrix.com. In preferred aspects the arrays are arrays of oligonucleotide probes of from length 15 to 100, more preferably from 20 to 50 and often from 20 to 30 bases in length. In preferred aspects the probes are arranged in features so that probes of the same sequence are present in the same feature. Many thousands, tens of thousands, hundreds of thousands or millions of different copies of a given probe sequence may be present in a feature. Depending on the method of synthesis of the probes on the array features will often contain non-full length probes that may be a portion of the desired sequence.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Pub. No. 20070065816, now abandoned, and U.S. Pat. Nos. 5,856,092, 6,300,063, 5,858,659, 6,284,460, 6,361,947, 6,368,799, 6,872,529 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070, which is incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603 each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Methods related to the paired-end tag strategy disclosed herein have been used to characterize fragments generated in chromosomal immunoprecipitation (ChIP) experiments using conventional sequencing (Wei et al., *Cell.* 2006 Jan. 13; 124(1):207-19), and to identify 5' and 3' termini of mRNA molecules using conventional sequencing (Ng et al., *Nucleic Acids Res.* 2006 Jul. 13; 34(12):e84).

Paired-end diTagging for transcriptome and genome analysis are disclosed in Ng et al. Curr Protoc Mol. Biol., Chapter 21 Unit 21.12 (2007). Software tools for managing paired-end diTag (PET) sequence data are disclosed, for example, in Chiu et al. BMC Bioinformatics, 2006, 25; 7:390.

US Patent publication Nos. 20060063158, 20050100911 and 20060183132 describe methods related to the hybrid selection methods disclosed herein and are incorporated herein by reference in their entireties.

Additional methods of sample preparation and techniques for reducing the complexity of a nucleic sample are described in Dong et al., *Genome Research* 11, 1418 (2001), in U.S. Pat. Nos. 6,361,947, 6,391,592, 6,632,611, 6,872,529, 6,958,225, 7,202,039 and U.S. Ser. No. 09/916,135, now abandoned.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel

*Methods in Enzymology*, Vol. 152, *Guide to Molecular Cloning Techniques* (Academic Press, Inc., San Diego, Calif., 1987); Young and Davism, *P.N.A.S.*, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625, in U.S. Ser. No. 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. No. 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2$^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Pub. Nos. US20020183936, 20070087368, 20040002818, 20030120432, 20040049354 and 20030100995.

b) Definitions

A "translocation" or "chromosomal translocation" is a chromosome abnormality caused by rearrangement of parts between nonhomologous chromosomes. It is detected on cytogenetics or a karyotype of affected cells. There are two main types, reciprocal (also known as non-Robertsonian) and Robertsonian. Also, translocations can be balanced (in an even exchange of material with no genetic information extra or missing, and ideally full functionality) or unbalanced (where the exchange of chromosome material is unequal resulting in extra or missing genes).

Reciprocal translocations are usually an exchange of material between nonhomologous chromosomes. They are found in about 1 in 600 human newborns. Such translocations are usually harmless and may be found through prenatal diagnosis. However, carriers of balanced reciprocal translocations have increased risks of creating gametes with unbalanced chromosome translocations leading to miscarriages or children with abnormalities.

A Robertsonian translocation is a type of rearrangement that involves two acrocentric chromosomes (chromosomes with very short p arms, in humans includes chromsomes 13, 14, 15, 21 and 22) that fuse near the centromere region with loss of the short arms. The resulting karyotype in humans leaves only 45 chromosomes since two chromosomes have fused together. A Robertsonian translocation involving chromosomes 13 and 14 is the most common translocation in human and is seen in about 1 in 1300 persons. Carriers of Robertsonian translocations are phenotypically normal, but there is a risk of unbalanced gametes which lead to miscarriages or abnormal offspring. For example, carriers of Robertsonian translocations involving chromosome 21 have a higher chance to have a child with Down syndrome.

There are a number of well characterized chromosomal abnormalities that lead to disease in humans. For example, Turner syndrome results from a single X chromosome (45, X or 45, X0). Klinefelter syndrome, the most common male chromosomal disease, otherwise known as 47, XXY is caused by an extra X chromosome. Edwards syndrome is caused by trisomy (three copies) of chromosome 18. Down syndrome, a common chromosomal disease, is caused by trisomy of chromosome 21. Patau syndrome is caused by trisomy of chromosome 13. Also documented are trisomy 8, trisomy 9 and trisomy 16, although they generally do not survive to birth.

There are a number of disorders that are known to arise from loss of just a piece of one chromosome. For example, Cri du chat (cry of the cat), from a truncated short arm on chromosome 5. 1p36 Deletion syndrome, from the loss of part of the short arm of chromosome 1. Angelman syndrome is characterized by about 50% of cases have a segment of the long arm of chromosome 15 missing. Chromosomal abnormalities can also occur in cancerous cells of an otherwise genetically normal individual. A well-documented example is the Philadelphia chromosome, a translocation mutation commonly associated with chronic myelogenous leukemia and less often with acute lymphoblastic leukemia.

Translocations are typically named according to the following: where t(A; B)(p1; q2) is used to denote a translocation between chromosome A and chromosome B. The information in the second set of parentheses, gives the precise location within the chromosome for chromosomes A and B respectively—with p indicating the short arm of the chromosome, q indicating the long arm, and the numbers after p or q refers to regions, bands and subbands seen when staining the chromosome.

A karyotype is the observed characteristics (number, type, shape etc) of the chromosomes of an individual or species. In normal diploid organisms, autosomal chromosomes are present in two identical copies, although polyploid cells have multiple copies of chromosomes and haploid cells have single copies. The chromosomes are arranged and displayed (often on a photo) in a standard format known as an idiogram: in pairs, ordered by size and position of centromere for chromosomes of the same size. Karyotypes are used to study chromosomal aberrations, and may be used to determine other macroscopically visible aspects of an individual's genotype, such as sex. In order to be able to see the chromosomes and determine their size and internal pattern, they are chemically labeled with a dye ("stained"). The pattern of individual chromosomes is called chromosome banding.

Normal human karyotypes contain 22 pairs of autosomal chromosomes and one pair of sex chromosomes. Normal karyotypes for women contain two X chromosomes and are typically denoted 46,XX; men have both an X and a Y chromosome denoted 46,XY.

In some embodiments of the presently disclosed methods one or more Type IIs restriction enzyme are used. Type IIs enzymes are a class of enzymes that cleave outside of their recognition sequence to one side. The specificity of cleavage is determined by the presence of the recognition site, but the site of actual cleavage can be variable. This provides an opportunity to "capture" unknown sequence. For example, the recognition site for MmeI (see U.S. Pat. No. 7,115,407) is:

```
5'  . . . TCCRAC(N)₂₀▽  . . . 3'         SEQ ID NO: 10

3'  . . . AGGYTG(N)₁₈△  . . . 5'         SEQ ID NO: 11
```

Another restriction enzyme that may be used is EcoP15I which has the following recognition site:

```
5'  . . . CAGCAG(N)₂₅▽  . . . 3'         SEQ ID NO: 12

3'  . . . GTCGTC(N)₂₇△  . . . 5'         SEQ ID NO: 13
```

Enzymes with relatively long N regions are preferable as the length of the "tag" is determined by the length of the N region and longer tags provide more information. Other enzymes that may be used include, for example, NmeAIII, BsgI, BpuEI, BpmI, AcuI, Eco57MI, Eco57I, GsuI, and CstMI. The length of the N region is preferably between 15 and 30 bases, for example 15, 16, 17, 18, 19, 20, 21, 22, 23, 24, 25, 26, 27, 28, 29 or 30 bases. Polishing the ends of the resulting fragments may result in filling in the overhang with complementary bases or removing the overhang, altering the length of the resulting tag accordingly. In some aspects two enzymes may be used and they may each result in a different tag length.

c) Methods for Detecting Translocations and Rearrangements

In one aspect, methods for detecting translocation events at the genome level are disclosed. In a first step (step 1), a pool of capture probes is created. The capture probe pool preferably consists of DNA fragments which are complimentary to the chromosome of interest, and which are labeled in such a way (e.g., biotinylated) that they can be captured on a solid surface (e.g., streptavidin-coated paramagnetic beads). Fragment sizes in the range of 50-250 bases are preferred, but other sizes, for example 200 to 1000, 500 to 2000 or 200 to 2000 may be used as well. The pool of DNA fragments may include, for example, whole genome amplified flow-sorted chromosomes, pooled ~10 kb LR-PCR amplicons generated using locus-specific primers, pooled PCR products generated using dU mediated amplification or pooled synthetic oligonucleotides corresponding to sequences within the chromosome of interest. Depending upon the preparation method, a single capture probe preparation preferably generates sufficient capture probe for 10 to 10,000 hybrid selection reactions. In another aspect the capture probe preparation may be amplified using a common set of primers.

In a next step, a tester sample is prepared (step 2). The tester sample consists of DNA fragments prepared from the sample to be analyzed such that the fragments collectively represent the entire genome of the DNA sample, and such that the fragments can all be amplified by PCR using a single set of PCR primers. The DNA fragments are prepared by fragmentation of genomic DNA to generate a desired range of double-stranded fragment sizes. Fragment sizes in the 100-1000 bp range are preferred, but other size ranges may also be used, for example, 200 to 2000 or 500 to 2000.

Methods that generate random double-stranded DNA fragments include hydrodynamic shearing, sonication, and DNAseI digestion in the presence of $Mn^{2+}$ or $Co^{2+}$ rather than $Mg^{2+}$ (all of these methods are preferably followed by treatment with T4 polymerase to create blunt ends). Alternatively, locus-specific fragmentation by restriction digestion can be performed. The fragmented dsDNA can then ligated to linkers containing universal primer binding sites, thereby enabling amplification of tester fragments using a single set of PCR primers. The fragments that are amplified are a representative subset of the genome of the starting sample.

In another aspect, Sigma's GenomPlex kit may be used to generate tester. The kit reliably converts genomic DNA into fragments with an average size of ~500 bp that are decorated with universal primer binding sites. See US Pat Pub 20030143599, 20040209299 and 20070031857.

Next, isolate and amplify tester fragments which hybridize to capture probes (step 3). The capture probe and tester fragments are hybridized together under conditions that result in the specific hybridization of tester fragments that are complimentary to the sequences in the capture probe. Because the tester fragments are derived from the entire genome, the molar concentration of the tester fragments can be relatively low (~10-100 fM). To ensure capture of cognate tester, it is preferably to include high molar concentrations (10-100 μM) of capture probe to drive the hybridization reaction, as well as to allow sufficient time (~48H) for capture. Also, in a preferred aspect, non-biotinylated Cot1 DNA may be included to block by competitive hybridization the capture of tester fragments containing repetitive elements.

The capture probes (as well as any hybridized tester fragments) are captured onto solid phase using e.g., streptavidin-coated paramagnetic beads (step 4). After washing the beads several times remove unhybridized tester fragments, the hybridized tester fragments are eluted from the beads by denaturation (step 5). The eluted tester fragments can then be PCR amplified using the tester-specific primers discussed in the previous section (step 6) in preparation for hybridization analysis.

In preferred aspects the amplified tester fragments from above are analyzed by hybridization to a tiling array to assay for chromosomal translocation. In the absence of a chromosomal rearrangement, the tester-specific PCR product should contain only amplified fragments complimentary to the capture probes. However, in the event of a chromosomal translocation, the PCR product will contain fragments derived from two different chromosomes: the chromosome assayed by the capture probe, and some other chromosome. To detect such events one can hybridize target prepared from the tester-specific PCR product onto a whole genome tiling array. The tester-specific PCR product is fragmented to 50-100 base fragments using DNAse I, and then end-labeled with biotin using TdT, following standard protocols. The resulting target is hybridized to a whole genome tiling array, and the array is stained and scanned, again following standard protocols.

The resulting hybridization pattern is then analyzed for evidence of translocation. Hybridization signal from array features corresponding to the chromosome targeted by the capture probe is indicative of successful positive selection during the hybrid selection process. By contrast, absence of hybridization signal from array features corresponding to chromosomes not targeted by the capture probe is indicative of successful negative selection during the hybrid selection process. Finally, the presence of hybridization signal from array features corresponding to chromosomes not targeted by the capture probe would be indicative of a translocation.

In another aspect, depending upon the size of the tester fragments subjected to the hybrid selection process, capture probes would not need to cover the entire chromosomal sequence, yet could still capture tester fragments covering the entire chromosome. For example, if the average size of tester fragments was 10 kb, then capture probes spaced every 5 kb could capture tester fragments covering the entire chromosome of interest. Similarly, 10 kb tester fragments would theoretically allow tiling probe densities of one probe pair (PM, MM) every 5 kb to detect virtually any translocation. This density would allow one to query the human genome with about 600,000 probe pairs (3E9/5E3=6E5). Higher density would ensure any translocation would be detected by multiple probe pairs, thereby enabling higher sensitivity and specificity.

The process described above enables one to assay for translocations involving a single chromosome with a single hybrid selection reaction and a single whole genome tiling array. The same methods may be applied to perform 24 separate hybrid selection reactions, one per chromosome, and assaying each of these on its own genome-wide tiling array, thus providing the ability to detect translocations between all possible pair-wise combinations of chromosomes. This approach has the added benefit of informational redundancy, i.e., a translocation between chromosomes 9 and 22 would be detected twice, once by the chromosome 9 hybrid selection reaction, and once by the chromosome 22 hybrid selection reaction. Moreover, the exact translocation breakpoint could be mapped to within the density of probes on the tiling array.

To reduce the number of reactions required to assay all possible chromosome combinations, multiple chromosomes may be assayed in a single hybrid selection reaction, and each chromosome can be assayed in multiple reactions, such that a unique assignment could be inferred from the data (e.g., see table 1 below).

TABLE 1

| | | Hybrid Selection Reaction | | | | | | | | | |
|---|---|---|---|---|---|---|---|---|---|---|---|
| | | 1 | 2 | 3 | 4 | 5 | 6 | 7 | 8 | 9 | 10 |
| Chromosome Assayed in Reaction | 1 | X | | | X | | | X | | | |
| | 2 | X | | | X | | | | X | | |
| | 3 | X | | | X | | | | | X | |
| | 4 | X | | | X | | | | | | X |
| | 5 | X | | | | X | X | | | | |
| | 6 | X | | | | X | | X | | | |
| | 7 | X | | | | X | | | X | | |
| | 8 | X | | | | X | | | | | X |
| | 9 | | X | | X | | | X | | | |
| | 10 | | X | | X | | | | X | | |
| | 11 | | X | | X | | | | | X | |
| | 12 | | X | | X | | | | | | X |
| | 13 | | X | | | X | X | | | | |
| | 14 | | X | | | X | | X | | | |
| | 15 | | X | | | X | | | X | | |
| | 16 | | X | | | X | | | | | X |
| | 17 | | | X | | | X | X | | | |
| | 18 | | | X | | | X | | X | | |
| | 19 | | | X | | | X | | | X | |
| | 20 | | | X | | | X | | | | X |
| | 21 | | | X | X | | | X | | | |
| | 22 | | | X | X | | | | X | | |
| | 23 | | | X | | X | | | | X | |
| | 24 | | | X | | X | | | | | X |

For example, if there is a translocation between chromosome 9 and chromosome 22, using the reactions in Table 1 it could be assigned from reactions 2 and 3. A translocation between chromosomes 1 and 2 could be assigned from reactions 7 and 8.

In another aspect, the detection and mapping of particular translocations can be targeted, rather than targeting the detection of all possible translocations genome-wide. This would be particularly valuable in contexts where patients may have a translocation involving a specific pair of chromosomes, but where the exact translocation breakpoint may vary from patient to patient. The methods disclosed herein may be combined with those disclosed in US 2006073511.

Detection of Rearrangements Using DITAGs.

In another aspect methods for detecting and analyzing genomic rearrangements using "ditag" methodology are disclosed. Ditags are disclosed, for example, in Wei et al., Cell 2006 Jan. 13; 124(1):207-19, and Ng et al., Nucleic Acids Res. 2006 Jul. 13; 34(12):e84, which are both incorporated herein by reference in their entireties for all purposes. In a first step "ditags" are generated from genomic DNA. In a preferred aspect, the sample prep is illustrated in FIG. 1. Digest a genomic DNA of interest with a restriction enzyme, e.g., a 6-cutter that produces a total of approximately 500,000 restriction fragments 101. The "tags" [103] and [105] are the sequences at the ends of the restriction fragments and can be predicted using genomic sequence databases and in silico digestion methods. The central portion of the restriction fragment is 104. Ligate the population of restriction fragments (RE frag or RE fragment) en masse into a "ditag plasmid backbone" 107 forming circles 108. In one embodiment the resulting library of circularized restriction fragments can be transformed into E. coli (provided the backbone 107 contains the required elements needed for reproduction in bacteria). The transformed bacteria may be used to amplify the material for subsequent steps. Exonuclease cleavage of non-circularized fragments may also be performed.

The ditag plasmid backbone 107 contains type IIs restriction enzyme (e.g., MmeI) sites flanking both ends of the restriction fragment cloning site so that cleavage occurs in the restriction fragment (sites of cleavage indicated by arrows). The ditag plasmid/restriction fragment DNA 108 is digested with the type IIs restriction enzyme, thereby separating the central portion of the restriction fragment 104 from the rest of 108. The tags 103 and 105 include the terminal 18 bp (when MmeI is used) from the ends of the restriction fragments. The length of the tags will vary depending on the type IIs enzyme used. The resulting fragment (includes 103, 107 and 105) is then circularized to form a circle 109 containing the ditags. The ditag is the combination of tags 103 and 105 joined together by ligation of the free ends. The ditags can be amplified, for example, using PCR amplification with primers 111 and 113 which are complementary to sequences in 107, to create ditag target 115, which contains all ditags from all restriction fragments from the genomic DNA. The amplified ditag target can be labeled during or after amplification, for example, by incorporation of a biotinylated, or otherwise labeled, nucleotide during synthesis or by end labeling using a terminal transferase. The ditag target can then be hybridized to a ditag sequencing array, described below, for analysis.

Figure 2:
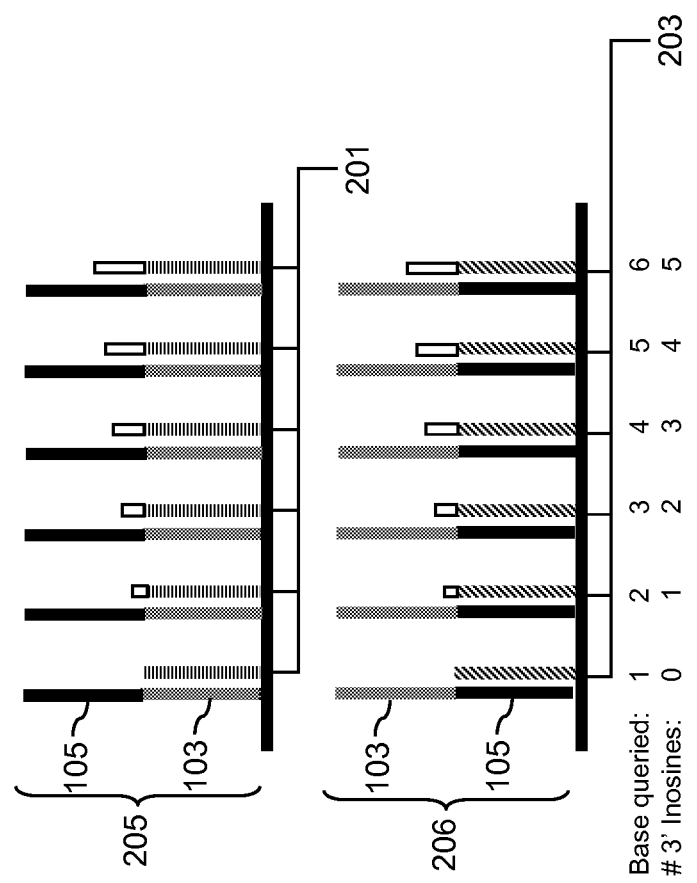
FIG. 2 shows ditag sequencing array features to query tags from one ditag.

In preferred aspects a ditag sequencing array is used for sequencing analysis. Given a set of about 500,000 restriction fragments containing 1 million tags (2 per fragment), having known sequences that are adjacent to the selected restriction site or sites, and given the possibility that a genomic rearrangement could bring any tag into the same restriction fragment as any other tag, to detect every possible combination of the about 1 million tags coupled to all other about 1 million tags using direct hybridization would require about 1 trillion probes. Reduction of the number of probes required for analysis may be achieved by using methods such as those shown in FIG. 2.

The ditag sequencing array (see FIG. 2) enables capture by hybridization of each of the 1M tags, using probes that are perfectly complementary to the tags, followed by determination of a number of bases of sequence from the adjacent tag in the ditag. The array shown in FIG. 2 determines 6 bases of the adjacent tag. This is accomplished using probe sets 201 and 203 specific for each strand of each tag 205 (forward tag) and 206 (reverse tag), where each probe set consists of 6 probes that have a portion that is complimentary to the captured tag. Probe set 201 is complementary to forward tag 205 while probe set 203 is complementary to the reverse tag 206. The 6 probes differ from one another in that they have from 0 to 5 inosine bases at their termini, shown in the figure as increasing length of the open square. This enables genotyping of 6 sequential bases in the hybridized tag 205 or 206, using either single-base extension of 3'-up probes or base-specific ligation to 5'-$PO_4$ probes. Each of the probes in the probe set can be used to determine one base in the unknown tag. For probe set 201 the unknown is the portion of the forward tag sequence corresponding to 105. For probe set 203 the unknown is the portion of the reverse tag sequence corresponding to 103. The lower portion of the probe is constant within probe set 201 or probe set 203 and is the complement of 103 and 105 respectively.

By determining 6 bases of information for each tag, one can distinguish between a maximum of $4^6$=4096 possible states. Thus, 6 bases of sequence should reduce the universe of possible mates from ~1M to ~1M/4K=~250. In addition, by comparing the 6 bases of sequence information with the sequence of the wild-type tag, one can determine with very high confidence whether the ditag is variant. Because the number of variant ditags in any given sample is expected to be a small fraction (e.g., <500) of the total ~500K tags, the total universe of variant tags that need be considered in a given sample will be a small subset (e.g., <1000) of all ~1M tags. As such, 6 bases of information per tag is likely sufficient to match most tags in variant ditags up with their mates. Moreover, if there are ambiguities, comparing sets of candidate tag mates for each tag across all variant tags, and identifying concordant mates between pairs of tags, should result in the determination of virtually all variant ditags with high confidence.

Ditag sequencing is performed to determine the identity of all ditags in the sample. The PCR product 115 is directly hybridized to the array in some aspects and may be about 55 to 120 base pairs, more preferably 70 to 100 and more preferably about 70 to 80 bp. In another aspect where shorter fragments are desired, the ditags may be liberated from the primer sequences in the PCR product 115 by digestion with a restriction enzyme. In some aspects the type IIs restriction enzyme used to separate the ditag plasmid from the rest of the restriction fragment 104 may be used. Thus, in preferred aspects the PCR product does not need to be digested with a non-sequence specific nuclease such as DNAseI and also does not require labeling prior to hybridization since the probes will preferably be labeled.

A 500,000 fragment ditag target would have a complexity of about 50 Mbp. Typically we have observed ~90% call rates and 99% accuracy from haploid genotyping (4 possible genotype states per position) of single base extension data generated from targets of this complexity. For diploid organisms, including humans, variant tag base calling is typically performed in the presence of wild-type tag sequence. However, this task is not nearly as difficult as de novo diploid genotyping (which must consider 10 possible genotype states per position), because the sequence of the wild-type allele is known, so only four genotype states are possible per position. Therefore, a 90% call rate and 99% accuracy should be approximately representative of the data quality we can expect from single base extension.

Figure 3:
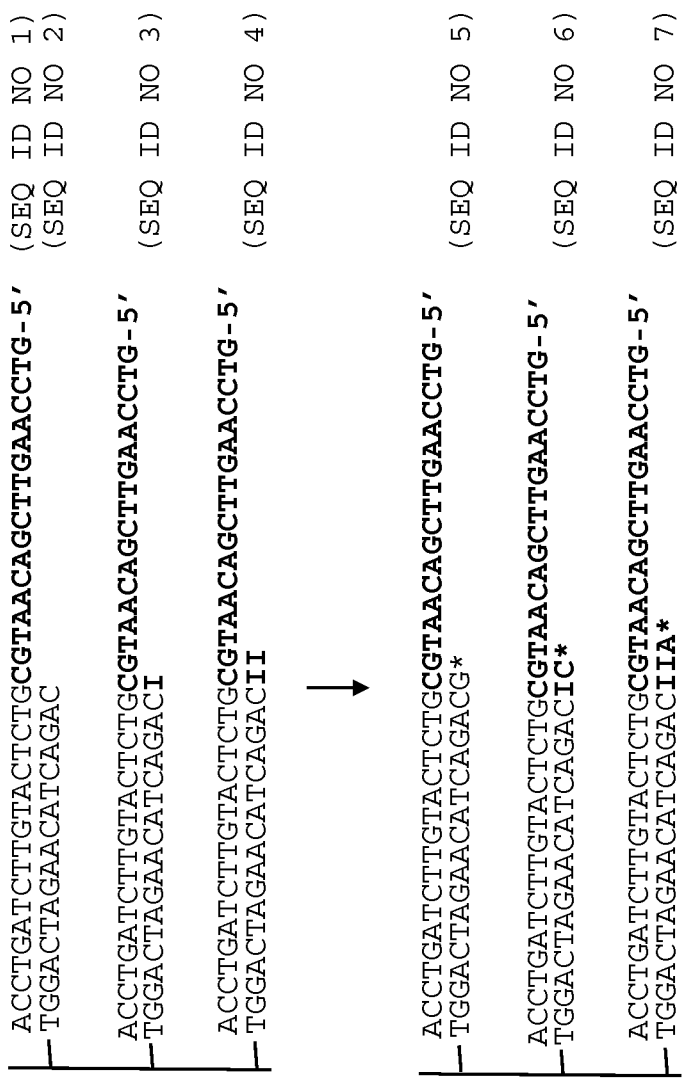
FIG. 3 shows examples of a ditag hybridized to three query tags with different numbers of inosines.

The single base extension method is shown in greater detail in FIG. 3. The ditag sequence (SEQ ID NO 1) is shown hybridized to 3 different probes (SEQ ID NO 2, 3 and 4) that are complementary to one of the tags (the 3' 18 bases of SEQ ID NO 1) and are designed to sequence individual positions in the second tag (the 5' 18 bases of SEQ ID NO 1). The probes are attached via their 5' ends so the 3' end is available for extension (or ligation). The first probe (SEQ ID NO 2) varies from the second probe (SEQ ID NO 3) by the addition in the second of a single inosine base (I) at the 3' end. The inosine can base pair with A, G, C or T, allowing interrogation of the second position of the second tag, G in this tag. The first probe interrogates the first position of the second tag, C in this tag. Template directed addition is used to add a single blocked, labeled nucleotide to the 3' end of the probes. The base that is added is the complement of the base opposite in the second tag sequences. Thus, a G is added to SEQ ID NO 2 resulting in SEQ ID NO 5 and indicating that the first base of the second tag is C. A C is added to SEQ ID NO 3 resulting in SEQ ID NO 6 and indicating that the second base of the second tag is G. An A is added to SEQ ID NO 4 resulting in SEQ ID NO 7 and indicating that the second base of the second tag is T. The labels are indicated by a * and in preferred aspects each label is specific for the base. The bases are preferably blocked from extension, for example, by using bases that are dideoxy or are otherwise blocked at the 3' position so that only a single base is added. Each probe is present at a different feature at a known or determinable location. Features have many hundreds, thousands, or more, copies of the same probe sequence.

In a preferred aspect the sequencing analysis uses 4-color single base extension or base specific ligation. Each of the bases (A, G, C and T) is labeled with a different distinguishable label so that the identity of the base that is incorporated into the probe can be determined and that can be used to determine the base present in the ditag at the complementary position. For example, if an A is incorporated into the probe then the ditag has a T at that position. In another aspect the assay may be performed using a single label and performing the extension or ligation reactions in separate parallel reactions on separate arrays each having a different base (A, G, C or T) present. A combination approach may also be used, for example, two different labels and two different arrays.

Data quality may degrade somewhat with single base extension from probes containing multiple inosines, but it is still sufficient for the definition of variant ditags as described above. If additional information content is desired, the number of bases sequenced can be increased beyond 6 bases of information.

FIG. 4 illustrates the same method shown in FIG. 1 but with example tag sequences at the ends of the fragment. The fragment 401 has double stranded tags at the ends. After ligation to the backbone sequence the construct shown in 403 is obtained. The arrows connect the restriction enzyme recognition site (RE) with the cleavage site (at the end of the arrow point). After cleavage with the RE the construct shown in 405 is obtained. The sequence on the left in 401 is still on the left but the orientation is flipped. After the second ligation, the construct of 407 is obtained. The left and right tags from 401 are now ligated together. The orientation is the same as in the original fragment but with the center portion removed. This fragment is then amplified.

The above example contemplates using ~500K restriction fragments, at an average fragment size of ~6K. This would allow mapping the breakpoint(s) of most genomic rearrangements from 1 kbp to within 6 kbp. The number of fragments can be reduced, reducing the number of tags that must be analyzed, by using a restriction enzyme that cuts the genome less frequently. The resolution of the method is reduced if larger fragments sizes are used. In another aspect a subset of the tags may be analyzed on the array. This also can result in a reduction in the sensitivity of the technique in proportion to the reduction in the number of tags being queried, for example, if one assays 100K of the 1M tags, one should expect to detect only ~10% of all possible genomic rearrangements.

The sequence of the tags can be predicted using genomic database information. In the absence of rearrangements the two ends of a given restriction fragment can be predicted from the genomic sequence. This is illustrated in FIG. 5. The arrows indicate cleavage sites for a restriction enzyme and the numbered regions to the left and right of the arrow head are the "tag" sequences corresponding to that restriction enzyme. So, for example, the first restriction site (a) is flanked by tag sequences 1 and 2. Cleavage at (a) and (b) generates fragment (i) having first end sequence (2) and second end sequence (3). The expected ditag for this fragment would have sequence 2 and 3 in the same ditag. If there was a rearrangement that deleted the restriction site (b) as illustrated in the lower panel, then fragment (i) would result in a different ditag that would have sequence 2 and 5 in the ditag. Probes to sequence 2 would detect sequence 5 as the adjacent sequence and probes to sequence 5 would detect sequence 2 as the adjacent sequence.

Arrays may also be designed to detect particular types of rearrangements directly by hybridization and without the need for extension or ligation. For example, to evaluate inversions only less than 100 kb in size, one need only consider ~1M tags times the ~20 other tags that might be mated with each tag by such a lesion. One could simply tile probes that are perfectly complementary to the ~20M possible ditags, label the PCR product containing the ditag and dispense with the requirement for single base extension.

Single base extension methods have been previously described in Syvannen, Nat Rev Genet. 2:930-942 (2001), for example. Ligation based sequencing methods have been previously described in, for example, EP723598. Methods for use of paired-end genomic signature tags for genome and epigenomic analysis are disclosed, for example, in Dunn et al., Genet Eng (NY) 28:159-73 (2007).

CONCLUSION

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

What is claimed is:

1. A method for analysis of genomic rearrangements in a sample from a genome comprising:
   (a) digesting the sample with a selected restriction enzyme to obtain restriction fragments that have a first end tag from a plurality of first end tags and a second end tag from a plurality of second end tags, with the first end tag and the second end tag flanking a central portion, wherein the sequences of the first end tags and the sequences of the second end tags have been determined by a computer;
   (b) ligating the restriction fragments to a common backbone fragment to form first circular molecules comprising restriction fragments and the common backbone, wherein the common backbone fragment has a first restriction enzyme recognition site for a first type IIS restriction enzyme at its first end and a second restriction enzyme recognition site for a second type ITS restriction enzyme at its second end;
   (c) cleaving the first circular molecule using the first type IIS restriction enzyme and the second type IIS restriction enzyme to form a plurality of first fragments, each comprising the backbone fragment flanked by a first end tag and a second end tag and a second fragment containing the central portion of the restriction fragment;
   (d) ligating the ends of the first fragments to form second circular molecules, wherein the ends of said first end tag and said second end tag in each fragment are ligated together to form a ditag, wherein each ditag comprises a first end tag and a second end tag that are immediately adjacent to one another in the ditag;
   (e) amplifying at least a portion of the second circular molecules using a pair of primers complementary to said backbone to obtain amplification target comprising amplified ditags;
   (f) hybridizing the amplification target to an array comprising at least 100,000 different ditag probes, wherein each ditag probe is perfectly complementary to a different first end tag from the plurality of first end tags, to obtain hybridized amplified ditags; and,
   (g) determining at least a partial sequence of the second end tag in a plurality of the hybridized amplified ditags, wherein the presence in a hybridized amplified ditag of a first end tag from a first fragment and a second end tag from a second different fragment indicates a genomic rearrangement.

2. The method of claim 1 wherein the partial sequence is at least 5 bases.

3. The method of claim 1 wherein the partial sequence is 6 bases.

4. The method of claim 1 wherein the partial sequence is at least 6 bases.

5. The method of claim 1 wherein the first type IIS restriction enzyme and the second type IIS restriction enzyme are the same type IIS restriction enzyme.

6. The method of claim 5 wherein the type IIS restriction enzyme is MmeI.

7. The method of claim 1 wherein the first end tag and the second end tag are each between 10 and 20 bases in length.

8. The method of claim 1 wherein the first end tag and the second end tag are each between 18 and 27 bases in length.

9. The method of claim 1 wherein for each base to be sequenced in the second end tag the array comprises a probe comprising the complement of the first end tag and between 2 and 5 inosines.

10. A method for detecting genomic rearrangements comprising:
    (a) fragmenting a genomic sample with a restriction enzyme to obtain restriction fragments each having a first terminal sequence and a second terminal sequence, said first and second terminal sequences being immediately adjacent to the cleavage site of the restriction enzyme;
    (b) ligating the restriction fragments each to a common backbone fragment, wherein said common backbone fragment includes a first and a second recognition site for a type IIs restriction enzyme, thereby forming first circular molecules each comprising said backbone fragment and one of said restriction fragments;
    (c) cutting said first circular fragments with said type IIs restriction enzyme to obtain ditag fragments comprising at least 10 bases of said first terminal sequence, at least 10 bases of said second terminal sequence and said common backbone fragment;
    (d) ligating the ends of said ditag fragments to form second circular molecules;
    (e) amplifying a portion of the second circular molecules wherein said portion includes the at least 10 bases of said first terminal sequence and at least 10 bases of said second terminal sequence, to obtain an amplification product;
    (f) analyzing said amplification product by hybridization to an array comprising at least 100,000 different support-bound probes wherein each probe is perfectly complementary to a different first terminal sequence and determining at least 5 bases of the sequence adjacent to the first terminal sequence to identify a plurality of combinations of first and second terminal sequences present in the same fragment;
    (g) comparing the results of (f) to predetermined combinations of first and second terminal sequences, wherein the predetermined combinations correspond to an absence of rearrangements, and wherein the combinations from (f) that do not match the predetermined combinations are indicative of genomic rearrangements.

11. The method of claim 10 wherein the expected combinations used in step (g) are from a database of ditag combinations predicted from in silico digestion of a genome.

12. A method for analysis of genomic rearrangements in a sample of genomic DNA comprising:
    (a) digesting the sample with a selected restriction enzyme to obtain restriction fragments;
    (b) ligating the first end of the restriction fragments to a first end of a common backbone fragment and a second end of the restriction fragments to a second end of the common backbone fragment thereby forming circular molecules that each comprise a restriction fragment and the common backbone fragment, wherein the common backbone fragment has a first restriction enzyme recognition site for a first type IIS restriction enzyme and a second restriction enzyme recognition site for a second type IIS restriction enzyme;
    (c) cleaving the first circular molecule using the first type IIS restriction enzyme and the second type IIS restriction enzyme to form a plurality of first fragments, each comprising the backbone fragment flanked by a first end tag and a second end tag and a second fragment containing the central portion of the restriction fragment;
    (d) ligating the ends of the first fragments to form second circular molecules, wherein the ends of said first end tag and said second end tag in each fragment are ligated together to form a ditag, wherein each ditag comprises a first end tag and a second end tag that are immediately adjacent to one another in the ditag;
    (e) amplifying at least a portion of the second circular molecules using a pair of primers complementary to said backbone to obtain amplification target comprising amplified ditags;
    (f) hybridizing the amplification target to an array comprising at least 100,000 different ditag probes, wherein each ditag probe is perfectly complementary to a different first end tag from the plurality of first end tags, to obtain hybridized amplified ditags; and,
    (g) determining at least a partial sequence of the second end tag in a plurality of the hybridized amplified ditags, wherein the presence in a hybridized amplified ditag of a first end tag from a first fragment and a second end tag from a second different fragment indicates a genomic rearrangement.

* * * * *

SEQUENCE LISTING

```
<160> NUMBER OF SEQ ID NOS: 13

<210> SEQ ID NO 1
<211> LENGTH: 36
<212> TYPE: DNA
<213> ORGANISM: homo sapiens

<400> SEQUENCE: 1
gtccaagttc gacaatgcgt ctcatgttct agtcca                            36

<210> SEQ ID NO 2
<211> LENGTH: 18
<212> TYPE: DNA
<213> ORGANISM: homo sapiens

<400> SEQUENCE: 2
tggactagaa catcagac                                                18

<210> SEQ ID NO 3
<211> LENGTH: 19
<212> TYPE: DNA
<213> ORGANISM: homo sapiens
<220> FEATURE:
<221> NAME/KEY: misc_feature
<222> LOCATION: (19)..(19)
<223> OTHER INFORMATION: n is a, c, g, or t
```

```
<400> SEQUENCE: 3
tggactagaa catcagacn                                              19

<210> SEQ ID NO 4
<211> LENGTH: 20
<212> TYPE: DNA
<213> ORGANISM: homo sapiens
<220> FEATURE:
<221> NAME/KEY: misc_feature
<222> LOCATION: (19)..(20)
<223> OTHER INFORMATION: n is a, c, g, or t

<400> SEQUENCE: 4
tggactagaa catcagacnn                                             20

<210> SEQ ID NO 5
<211> LENGTH: 19
<212> TYPE: DNA
<213> ORGANISM: homo sapiens

<400> SEQUENCE: 5
tggactagaa catcagacg                                              19

<210> SEQ ID NO 6
<211> LENGTH: 20
<212> TYPE: DNA
<213> ORGANISM: homo sapiens
<220> FEATURE:
<221> NAME/KEY: misc_feature
<222> LOCATION: (19)..(19)
<223> OTHER INFORMATION: n is a, c, g, or t

<400> SEQUENCE: 6
tggactagaa catcagacnc                                             20

<210> SEQ ID NO 7
<211> LENGTH: 21
<212> TYPE: DNA
<213> ORGANISM: homo sapiens
<220> FEATURE:
<221> NAME/KEY: misc_feature
<222> LOCATION: (19)..(20)
<223> OTHER INFORMATION: n is a, c, g, or t

<400> SEQUENCE: 7
tggactagaa catcagacnn a                                           21

<210> SEQ ID NO 8
<211> LENGTH: 20
<212> TYPE: DNA
<213> ORGANISM: homo sapiens

<400> SEQUENCE: 8
actctggtgt cgattcctgg                                             20

<210> SEQ ID NO 9
<211> LENGTH: 19
<212> TYPE: DNA
<213> ORGANISM: homo sapiens

<400> SEQUENCE: 9
caggaatcga caccagagt                                              19

<210> SEQ ID NO 10
<211> LENGTH: 26
```

```
<212> TYPE: DNA
<213> ORGANISM: homo sapiens
<220> FEATURE:
<221> NAME/KEY: misc_feature
<222> LOCATION: (7)..(26)
<223> OTHER INFORMATION: n is a, c, g, or t

<400> SEQUENCE: 10
tccracnnnn nnnnnnnnnn nnnnnn                                              26

<210> SEQ ID NO 11
<211> LENGTH: 24
<212> TYPE: DNA
<213> ORGANISM: homo sapiens
<220> FEATURE:
<221> NAME/KEY: misc_feature
<222> LOCATION: (1)..(18)
<223> OTHER INFORMATION: n is a, c, g, or t

<400> SEQUENCE: 11
nnnnnnnnnn nnnnnnnngt ygga                                                24

<210> SEQ ID NO 12
<211> LENGTH: 31
<212> TYPE: DNA
<213> ORGANISM: homo sapiens
<220> FEATURE:
<221> NAME/KEY: misc_feature
<222> LOCATION: (7)..(31)
<223> OTHER INFORMATION: n is a, c, g, or t

<400> SEQUENCE: 12
cagcagnnnn nnnnnnnnnn nnnnnnnnnn n                                        31

<210> SEQ ID NO 13
<211> LENGTH: 33
<212> TYPE: DNA
<213> ORGANISM: homo sapiens
<220> FEATURE:
<221> NAME/KEY: misc_feature
<222> LOCATION: (1)..(27)
<223> OTHER INFORMATION: n is a, c, g, or t

<400> SEQUENCE: 13
nnnnnnnnnn nnnnnnnnnn nnnnnnnctg ctg                                      33
```